US008935891B2

(12) United States Patent
Taoufik et al.

(10) Patent No.: US 8,935,891 B2
(45) Date of Patent: Jan. 20, 2015

(54) OLEFIN METATHESIS CATALYST CONTAINING TUNGSTEN FLUORINE BONDS

(75) Inventors: Mostafa Taoufik, Villeurbanne (FR); Etienne Mazoyer, Lyons (FR); Christopher P Nicholas, Evanston, IL (US); Jean-Marie Basset, Caluire (FR)

(73) Assignee: UOP LLC, Des Plaines, IL (US)

( * ) Notice: Subject to any disclaimer, the term of this patent is extended or adjusted under 35 U.S.C. 154(b) by 310 days.

(21) Appl. No.: 13/156,860

(22) Filed: Jun. 9, 2011

(65) Prior Publication Data
US 2012/0316057 A1 Dec. 13, 2012

(51) Int. Cl.
B01J 31/12 (2006.01)
B01J 31/22 (2006.01)
C07F 11/00 (2006.01)
B01J 37/06 (2006.01)
B01J 21/08 (2006.01)
B01J 23/30 (2006.01)
B01J 35/10 (2006.01)
B01J 37/02 (2006.01)
C07C 6/04 (2006.01)
C07F 7/02 (2006.01)

(52) U.S. Cl.
CPC ............ *B01J 31/2295* (2013.01); *C07F 11/00* (2013.01); *B01J 37/06* (2013.01); *B01J 21/08* (2013.01); *B01J 23/30* (2013.01); *B01J 35/1014* (2013.01); *B01J 35/1019* (2013.01); *B01J 37/0209* (2013.01); *C07C 6/04* (2013.01); *B01J 31/2208* (2013.01); *C07F 7/02* (2013.01); *C07C 2521/08* (2013.01); *C07C 2531/22* (2013.01)
USPC .................. 52/155; 556/9; 502/152; 502/305

(58) Field of Classification Search
None
See application file for complete search history.

(56) References Cited

U.S. PATENT DOCUMENTS

| 2,620,314 | A |  | 12/1952 | Hoekstra |  |
|---|---|---|---|---|---|
| 3,274,124 | A |  | 9/1966 | O'Hara |  |
| 3,761,427 | A |  | 9/1973 | Regier |  |
| 3,909,450 | A |  | 9/1975 | O'Hara |  |
| 3,978,150 | A |  | 8/1976 | McWilliams, Jr. |  |
| 4,217,244 | A |  | 8/1980 | Montgomery |  |
| 4,288,688 | A |  | 9/1981 | Kiyama et al. |  |
| 4,575,575 | A |  | 3/1986 | Drake et al. |  |
| 4,663,304 | A |  | 5/1987 | Drake et al. |  |
| 4,727,198 | A | * | 2/1988 | Spencer | 568/482 |
| 4,988,659 | A |  | 1/1991 | Pecoraro |  |
| 5,026,935 | A |  | 6/1991 | Leyshon et al. |  |
| 5,026,936 | A |  | 6/1991 | Leyshon et al. |  |
| 5,082,909 | A |  | 1/1992 | Bell |  |
| 5,304,692 | A |  | 4/1994 | Yamada et al. |  |
| 5,905,055 | A | * | 5/1999 | Verdonck et al. | 502/311 |
| 5,914,433 | A |  | 6/1999 | Marker |  |
| 6,177,381 | B1 |  | 1/2001 | Jensen et al. |  |
| 6,683,019 | B2 |  | 1/2004 | Gartside et al. |  |
| 6,727,396 | B2 |  | 4/2004 | Gartside |  |
| 6,777,582 | B2 |  | 8/2004 | Gartside et al. |  |
| 6,858,133 | B2 |  | 2/2005 | Dath et al. |  |
| 6,867,341 | B1 |  | 3/2005 | Abrevaya et al. |  |
| 6,977,318 | B2 |  | 12/2005 | Bridges |  |
| 7,074,976 | B2 |  | 7/2006 | Powers et al. |  |
| 7,087,155 | B1 |  | 8/2006 | Dath et al. |  |
| 7,214,841 | B2 |  | 5/2007 | Gartside et al. |  |
| 7,268,265 | B1 |  | 9/2007 | Stewart et al. |  |
| 7,375,257 | B2 |  | 5/2008 | Dath et al. |  |
| 7,396,798 | B2 |  | 7/2008 | Ma et al. |  |
| 7,586,018 | B2 |  | 9/2009 | Bozzano et al. |  |
| 2007/0191212 | A1 |  | 8/2007 | Schubert et al. |  |
| 2007/0225478 | A1 |  | 9/2007 | Querci et al. |  |
| 2009/0264672 | A1 | * | 10/2009 | Abraham et al. | 560/190 |
| 2012/0316374 | A1 |  | 12/2012 | Taoufik et al. |  |

FOREIGN PATENT DOCUMENTS

| CN | 101190869 A | 6/2008 |
| EP | 0276096 A1 | 7/1988 |
| EP | 480447 A2 * | 4/1992 |

OTHER PUBLICATIONS

Warren, alpha-Hydrogen Migration Reactions in Tungsten (VI) cyclopentadienyl alkylidyne complexes, Journal of Organometallic Chemistry, vol. 569, Issues 102, Oct. 30, 1998 (125-137).*
Geyer, Andrea M., et al., Synthetic, mechanistic, and Computational investigations of Nitrile-Alkyne Cross-Metathesis, J. Am. chem. Soc., 130, 8984-8999 (2008).*
Schrock et al., Aqueous Tungsten (VI) Alkyl Chemistry, Journal of the American Chemical Society, 1983, pp. 7176-7177, vol. 105.
Schrock et al., A Molecule Containing the OWOWO Unit. Synthesis, Structure, and Spectroscopy, Journal of the American Chemical Society, 1984, pp. 6305-6310, vol. 106.
U.S. Appl. No. 12/701,508, filed Feb. 5, 2010, Krawczyk et al.
Sanford et al., "Mechanism and Activity of Ruthenium Olefin Metathesis Catalysts", J. Am. Chem. Soc, 2001, 123, pp. 6543-6554.
Straub, "Ligand Influence on Metathesis Activity of Ruthenium Carbene Catalysts: A DFT Study", Adv. Synth. Catal., 2007, 349, pp. 204-214.
Dias et al., "Well-Defined Ruthenium Olefin Metathesis Catalysts: Mechanism and Activity", J. Am. Chem. Soc., 1997, 119, pp. 3887-3897.

(Continued)

*Primary Examiner* — Melissa Swain

(57) ABSTRACT

A catalyst for the metathesis of olefins in general and specifically for the production of propylene from ethylene and butylene has been developed. The catalyst comprises a tungsten metal compound, which contains at least one tungsten-fluoro bond, dispersed or grafted onto a support. A specific example of the catalyst is the compound $WOF(CH_2CMe_3)_3$ grafted onto a silica support.

8 Claims, No Drawings

(56) References Cited

OTHER PUBLICATIONS

Fagnou, "Halide Effects in Transition Metal Catalysis", Angew. Chem. Int. Ed. 2002, 41, 26-47.
Balcar, "Re(VII) oxide on mesoporous alumina of different types—Activity in the metathesis of olefins and their oxygen-containing derivatives", Applied Catalysis A: General 320 (2007) 56-63.
Guo, "Olefin Metathesis Over Molybdenum and Tungsten Catalysts Immobilized on Inorganic Carriers", Cuihua Xuebao, 7(2) 177-82 (1986) Chem. Abstr. No. 99499 V105 N. 12. Language: Chinese [abstract].
Handzlik, "Active sites of olefin metathesis on molybdena-alumina system: A periodic DFT study", Journal of Catalysis 256 (2008) 1-14.
Hu, "Synthesis and characterization of tungsten-substituted SBA-15: An enhanced catalyst for 1-butene metathesis", Microporous and Mesoporous Materials 93 (2006) 158-163.
Huang, "The effect of calcination time on the activity of WO3/Al2O3/HY catalysts for the metathesis reaction between ethene and 2-butene", Applied Catalysis A: General 323 (2007) 94-103.
Huang, "The influence of preparation procedures and tungsten loading on the metathesis activity of ethene and 2-butene over supported WO3 catalysts", Journal of Molecular Catalysis A: Chemical 267 (2007) 224-233.
Janowski, "(In the) Metathesis of Propylene on WO3/SiO2 and MOO3/SiO2 Catalysts", Chem. Tech. (Leipz.) V29 N.6 313-18 (Jun. 1977). Language: German [abstract].
Lokhat, "Gas-phase metathesis of 1-hexene over a WO3/SiO2 catalyst: Search for optimal reaction conditions", Applied Catalysis A: General 351 (2008) 137-147.
Suzuki, "Selective Chain Propagation of Ethene to Propene on Silica Supported Cobalt Catalyst", 2007 AIChe (American Institute of Chemical Engineers) Annual Meeting, Salt Lake City, Utah, USA.
Van Schalkwyk, "Factors that could influence the activity of a WO3/SiO2 Catalyst: Part III", Applied Catalysis A: General 255 (2003) 143-152.
Wang, "Synthesis and characterization of highly efficient tungsten-substituted SBA-15 catalysts for olefin metathesis", World Petroleum Congress Proceedings 2006, p. 3, 18th World Petroleum Congress, 2006, Johnnesburg Energy Institute.
Zama, "Propene metathesis reaction on di- and trinuclear molybdenum complexes grafted on mesoporous FSM-16 and silica. Structural characterization and their catalytic performances", Applied Catalysis A: General 194-195 (2000) 285-296.

\* cited by examiner

OLEFIN METATHESIS CATALYST CONTAINING TUNGSTEN FLUORINE BONDS

FIELD OF THE INVENTION

This invention relates to a catalyst for the metathesis of olefins in general and specifically for the production of propylene from ethylene and butylene.

DESCRIPTION OF RELATED ART

Propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. Currently, the majority of propylene is produced during the steam cracking or pyrolysis of hydrocarbon feedstocks such as natural gas, petroleum liquids, and carbonaceous materials (e.g., coal, recycled plastics, and organic materials). The major product of steam cracking, however, is generally ethylene and not propylene.

Steam cracking involves a very complex combination of reaction and gas recovery systems. Feedstock is charged to a thermal cracking zone in the presence of steam at effective conditions to produce a pyrolysis reactor effluent gas mixture. The mixture is then stabilized and separated into purified components through a sequence of cryogenic and conventional fractionation steps. Generally, the product ethylene is recovered as a low boiling fraction, such as an overhead stream, from an ethylene/ethane splitter column requiring a large number of theoretical stages due to the similar relative volatilities of the ethylene and ethane being separated. Ethylene and propylene yields from steam cracking and other processes may be improved using known methods for the metathesis or disproportionation of $C_4$ and heavier olefins, in combination with a cracking step in the presence of a zeolitic catalyst, as described, for example, in U.S. Pat. No. 5,026,935 and U.S. Pat. No. 5,026,936. The cracking of olefins in hydrocarbon feedstocks, to produce these lighter olefins from $C_4$ mixtures obtained in refineries and steam cracking units, is described in U.S. Pat. No. 6,858,133; U.S. Pat. No. 7,087,155; and U.S. Pat. No. 7,375,257.

Steam cracking, whether or not combined with conventional metathesis and/or olefin cracking steps, does not yield sufficient propylene to satisfy worldwide demand. Other significant sources of propylene are therefore required. These sources include by-products of fluid catalytic cracking (FCC) and resid fluid catalytic cracking (RFCC), normally targeting gasoline production. FCC is described, for example, in U.S. Pat. No. 4,288,688 and elsewhere. A mixed, olefinic $C_3/C_4$ by-product stream of FCC may be purified in propylene to polymer grade specifications by the separation of $C_4$ hydrocarbons, propane, ethane, and other compounds.

Much of the current propylene production is therefore not "on purpose," but as a by-product of ethylene and gasoline production. This leads to difficulties in coupling propylene production capacity with its demand in the marketplace. Moreover, much of the new steam cracking capacity will be based on using ethane as a feedstock, which typically produces only ethylene as a final product. Although some hydrocarbons heavier than ethylene are present, they are generally not produced in quantities sufficient to allow for their recovery in an economical manner. In view of the current high growth rate of propylene demand, this reduced quantity of co-produced propylene from steam cracking will only serve to accelerate the increase in propylene demand and value in the marketplace.

A dedicated route to light olefins including propylene is paraffin dehydrogenation, as described in U.S. Pat. No. 3,978,150 and elsewhere. However, the significant capital cost of a propane dehydrogenation plant is normally justified only in cases of large-scale propylene production units (e.g., typically 250,000 metric tons per year or more). The substantial supply of propane feedstock required to maintain this capacity is typically available from propane-rich liquefied petroleum gas (LPG) streams from gas plant sources. Other processes for the targeted production of light olefins involve high severity catalytic cracking of naphtha and other hydrocarbon fractions. A catalytic naphtha cracking process of commercial importance is described in U.S. Pat. No. 6,867,341.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such processes may be improved using olefin cracking to convert some or all of the $C_4^+$ product of MTO in an olefin cracking reactor, as described in U.S. Pat. No. 7,268,265. An oxygenate to light olefins conversion process in which the yield of propylene is increased through the use of dimerization of ethylene and metathesis of ethylene and butylene, both products of the conversion process, is described in U.S. Pat. No. 7,586,018.

Despite the use of various dedicated and non-dedicated routes for generating light olefins industrially, the demand for propylene continues to outpace the capacity of such conventional processes. Moreover, further demand growth for propylene is expected. A need therefore exists for cost-effective methods that can increase propylene yields from both existing refinery hydrocarbons based on crude oil as well as non-petroleum derived feed sources.

SUMMARY OF THE INVENTION

This invention relates to a catalyst for the metathesis of olefins. Accordingly one embodiment of the invention is a catalyst comprising a tungsten metal compound characterized in that it contains at least one tungsten-fluorine bond, the compound dispersed on a refractory oxide support wherein the compound is chemically bonded to the support.

These and other objects, embodiments and details of this invention will become apparent after a detailed description of the invention.

DETAILED DESCRIPTION OF THE INVENTION

As stated, this invention relates to a catalyst for the metathesis of olefins. The catalyst comprises a tungsten metal compound having at least one tungsten-fluorine bond which is dispersed on a refractory oxide support and the compound is chemically bonded to the support. Accordingly, one necessary component of the invention is a tungsten metal compound with at least one tungsten-fluorine bond. The tungsten metal compound has the empirical formula of: $WR_4F$, $WOFR_3$ or $W(NR')FR_3$, where R is an organic group which does not have any hydrogen atoms beta to the tungsten, non-limiting examples of which are neopentyl ($-CH_2CMe_3$); methyl, 2,2-diethylpropyl ($-CH_2C(CH_2CH_3)_2Me$), and 2,2- diethylbutyl (—$CH_2C(CH_2CH_3)_2CH_2CH_3$). R' is an organic group such as but not limited to H, phenyl, 2,6-dimethylphenyl and methyl. The oxo compound can be synthesized by first reacting O=$WCl_4$ with an alkylating agent such as $RMgCl$, RLi, RNa or RK to give O=$WR_3Cl$ which is then reacted with a fluorinating agent such as $AgBF_4$, HF or NaF to form the O=$WR_3F$ compound. The reaction product is treated with a base to remove $BF_3$ impurities, such as but not limited to $NR''_3$ where non-limiting examples of R'' include H, methyl, ethyl, and phenyl. The overall process can be summarized as follows where R is neopentyl and R'' is ethyl.

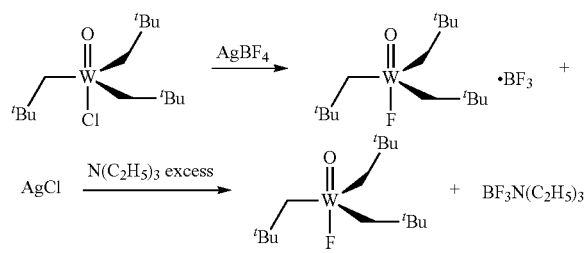

An alternate way to synthesize the oxo tungsten fluoro compound is to react (O=W—O—W=O) $R_6$ with a fluorinating agent (same as above) to produce O=$WR_3F$. Synthesis of (O=W—O—W=O) $R_6$ is described in J. AMER. CHEM. SOC., 1983, vol. 105, 7176-7 which is incorporated by reference in its entirety.

To synthesize the imido compound, often the starting O=$WCl_4$ compound is reacted with R' isocyanate, to yield $CO_2$ and R'N=$WCl_4$ followed by alkylation and fluorination as above. An example of this synthesis is diagrammatically shown below.

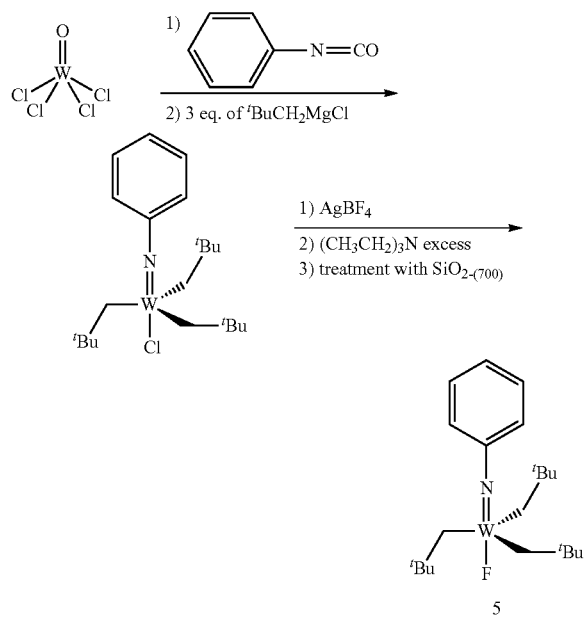

Alternatively, $NH_3$ can be used in place of R' isocyanate to yield HN=$WCl_4$ and $H_2O$. As shown in the above equation, if all the boron is not removed, it can be removed by treatment with silica.

Having obtained the tungsten-fluorine bond containing compound, it is now dispersed or grafted onto an inorganic refractory support. Suitable inorganic refractory supports which can be used include, but are not limited to, silica, aluminas, silica-alumina, zirconia, titania, etc. with silica being preferred. Mixtures of refractory oxides can also be used and fall within the bounds of the invention. The support generally has a surface area from about 50 to 1000 $m^2/g$, and preferably from about 80 to about 500 $m^2/g$. It should be pointed out that silica-alumina is not a physical mixture of silica and alumina but means an acidic and amorphous material that has been cogelled or coprecipitated. This term is well known in the art, see e.g., U.S. Pat. No. 3,909,450, U.S. Pat. No. 3,274,124 and U.S. Pat. No. 4,988,659, all of which are incorporated by reference in their entirety. Additionally, naturally occurring silica-aluminas such as attapulgite clay, montmorillonite clay or kieselguhr are within the definition of silica-alumina.

Although the supports can be used as powders, it is preferred to form the powder into shaped articles. Examples of shaped articles include but are not limited to spheres, pills, extrudates, irregularly shaped particles and tablets. Methods of forming these various articles are well known in the art. The support can also be in the form of a layer on an inert core such as described in U.S. Pat. No. 6,177,381 which is incorporated by reference in its entirety.

Spherical particles may be formed, for example, from the preferred alumina by: (1) converting the alumina powder into an alumina sol by reaction with a suitable peptizing acid and water and thereafter dropping a mixture of the resulting sol and a gelling agent into an oil bath to form spherical particles of an alumina gel which are easily converted to a gamma-alumina support by known methods; (2) forming an extrudate from the powder by established methods and thereafter rolling the extrudate particles on a spinning disk until spherical particles are formed which can then be dried and calcined to form the desired particles of spherical support; and (3) wetting the powder with a suitable peptizing agent and thereafter rolling the particles of the powder into spherical masses of the desired size.

Instead of peptizing an alumina powder, spheres can be prepared as described in U.S. Pat. No. 2,620,314 which is incorporated by reference in its entirety. The first step in this method involves forming an aluminum hydrosol by any of the techniques taught in the art and preferably by reacting aluminum metal with hydrochloric acid. The resultant hydrosol is combined with a suitable gelling agent such as hexamethylene tetraamine (HMT). The resultant, mixture is dropped into an oil bath which is maintained at a temperature of about 90° to about 100° C. The droplets of the mixture remain in the oil bath until they set and form hydrogel spheres. Next the spheres are continuously withdrawn from the oil, bath and treated with an ammoniacal solution at a temperature of about 80° to about 95° C. for a time of about 2 to about 2.5 hours. After treatment with the ammoniacal solution, the spheres are dried at a temperature of about 80° to about 150° C. and then calcined at a temperature of about 400° to about 700° C. for a time of about 1 to about 24 hours.

Extrudates are prepared by mixing the inorganic hydroxide or oxide with water and suitable peptizing agents such as nitric acid, acetic acid, etc. until an extrudable dough is formed. The resulting dough is then extruded through a suitably sized die to form extrudate particles. The extrudate particles are dried at a temperature of about 150° to about 200° C. and then calcined at a temperature of about 450° to about 800° C. for a period of about 0.5 to about 10 hours to effect the preferred form of the refractory inorganic oxide.

A preferred support is silica with amorphous silica being one type of silica. Examples include Davisil®46, Davisil®636 (W.R. Grace & Co., Columbia, Md.) and other precipitated silicas. Regardless of the source, the silica will have a surface area, either as received or after an optional acid washing step in the catalyst preparation procedure, of at least about 50 m$^2$/g and preferably from about 80 to about 500 m$^2$/g, and most preferably from about 400 to about 500 m$^2$/g. Another form of silica which can be used is any of the crystalline mesoporous silicas which are defined to be virtually pure silica. These include materials such as MCM-41 and SBA-15. Additional forms of silica are zeolites which are defined to be virtually pure silica. Zeolites are crystalline aluminosilicate compositions which are microporous and which are formed from corner sharing AlO$_2$ and SiO$_2$ tetrahedra. By virtually pure silica zeolites is meant that virtually all the aluminum has been removed from the framework. It is well known that it is virtually impossible to remove all the aluminum. Numerically, a zeolite is virtually pure silica when the Si/Al ratio has a value of at least 3,000, preferably 10,000 and most preferably 20,000.

The silica described above can optionally be acid washed (see U.S. patent application Ser. No. 12/701,508 which is incorporated by reference in its entirety) to further improve the properties of the resulting catalyst. Acid washing involves contacting the silica with an acid, including an organic acid or an inorganic acid. Particular inorganic acids include nitric acid, sulfuric acid, and hydrochloric acid, with nitric acid and hydrochloric acid being preferred. The acid concentration in aqueous solution, used for the acid washing, is generally in the range from about 0.05 molar (M) to about 3 M, and often from about 0.1 M to about 1 M. The acid washing can be performed under static conditions (e.g., batch) or flowing conditions (e.g., once-through, recycle, or with a combined flow of make-up and recycle solution).

Representative contacting conditions for acid washing the silica support include a temperature generally from about 20° C. (68° F.) to about 120° C. (248° F.), typically from about 30° C. (86° F.) to about 100° C. (212° F.), and often from about 50° C. (122° F.) to about 90° C. (194° F.). The contacting time is generally from about from about 10 minutes to about 5 hours, and often from about 30 minutes to about 3 hours. It has been determined that acid washing increases the BET surface area of the silica support at least 5% (e.g., from about 5% to about 20%), and often at least 10% (e.g., from about 10% to about 15%). For zeolitic forms of silica, acid washing decreases the amount of aluminum in the framework, i.e. increases the Si/Al ratio. A third effect of acid washing is a decrease in the average pore diameter of the silica support. In general, the pore diameter is decreased by at least about 5%, and often by at least about 10%.

The tungsten-fluoro compound is now grafted onto the desired support by one of several techniques including contacting the support with a solution containing the tungsten-support, sublimation of the tungsten compound onto the support and direct contacting of the tungsten compound with the desired support. When the tungsten compound is contacted with the support using a solution, the compound is first dissolved in an appropriate solvent. Solvents which can be used to dissolve the compound include but are not limited to diethylether, pentane, benzene, and toluene depending on the R groups and compound reactivity. Contacting is carried out at a temperature of about −100° to about 80° C., preferably at a temperature of about −75° to about 35° C. for a time of about 5 minutes to about 24 hours and preferably for a time from about 15 minutes to about 4 hours. The amount of tungsten-fluoro compound dispersed on the support can vary widely but is usually from about 0.5 to about 10 wt-% of the catalyst (support plus compound) as the metal. Preferably the amount of compound is from about 1.5 to about 7 wt-%.

For sublimation, the tungsten compound is sublimed under dynamic vacuum (typically less than 10$^{-3}$ torr) onto the support by heating the tungsten compound at a temperature of about 30° to about 150° C. The support is then heated to a temperature of about 30° to about 150° C. for about 1 to 4 hours, and the excess of the tungsten compound is removed by reverse sublimation at a temperature of about 30° to about 150° C. and condensed into a cooled area.

For the direct contact method of grafting the tungsten compound onto the support, the tungsten compound and the support are stirred at a temperature of about −10° to about 100° C. for a time of about 2 to about 6 hours under an inert atmosphere, e.g. argon. All volatile compounds are condensed into another reactor. A solvent such as pentane is then introduced into the reactor by distillation, and the solid is washed three times with the solvent e.g. pentane via filtration-condensation cycles. After evaporation of the solvent, the catalyst powder is dried under vacuum. Without being bound by theory, it is thought that regardless of the preparation method, hydroxyls on the support surface react with W—R bond(s) to form W—O— support bonds, with concomitant release of RH.

The catalyst of the invention is useful as a metathesis catalyst. Olefin metathesis (or disproportionation) processes involve contacting a hydrocarbon feedstock with the catalyst described above at metathesis reaction conditions. The hydrocarbon feedstock refers to the total, combined feed, including any recycle hydrocarbon streams, to the catalyst in the metathesis reactor or reaction zone, but not including any non-hydrocarbon gaseous diluents (e.g., nitrogen), which may be added along with the feed according to some embodiments. The hydrocarbon feedstock may, but does not necessarily, comprise only hydrocarbons. The hydrocarbon feedstock generally comprises predominantly (i.e., at least 50% by weight) hydrocarbons, typically comprises at least about 80% (e.g., from about 80% to about 100%) hydrocarbons, and often comprises at least about 90% (e.g., from about 90% to about 100% by weight) hydrocarbons.

Also, in olefin metathesis processes according to the present invention, the hydrocarbons contained in the hydrocarbon feedstock are generally predominantly (i.e., at least 50% by weight, such as from about 60% to about 100% by weight) olefins, typically they comprise at least about 75% (e.g., from about 75% to about 100%) by weight olefins, and often they comprise at least about 85% (e.g., from about 85% to about 100% or from about 95% to about 100%) by weight olefins. In other embodiments, these amounts of olefins are representative of the total olefin percentages in the hydrocarbon feedstock itself, rather than the olefin percentages of the hydrocarbons in the hydrocarbon feedstock. In yet further embodiments, these amounts of olefins are representative of the total percentage of two particular olefins in the hydrocarbon feedstock, having differing carbon numbers, which can combine in the metathesis reactor or reaction zone to produce a third olefin having an intermediate carbon number (i.e., having a carbon number intermediate to that of (i) a first olefin (or first olefin reactant) and (ii) a second olefin (or second olefin reactant) having a carbon number of at least two greater than that of the first olefin). In general, the two olefins are present in the hydrocarbon feedstock to the metathesis reactor in a molar ratio of the first olefin to the second olefin from about 0.2:1 to about 10:1, typically from about 0.5:1 to about 3:1, and often from about 1:1 to about 2:1.

In an exemplary embodiment, the two olefins (first and second olefins) of interest are ethylene (having two carbons) and butylene (having four carbons), which combine in the metathesis reactor or reaction zone to produce desired propylene (having three carbons). The term "butylene" is meant to encompass the various isomers of the $C_4$ olefin butene, namely butene-1, cis-butene-2, trans-butene-2, and isobutene. In the case of metathesis reactions involving butylene, it is preferred that the butylene comprises predominantly (i.e., greater than about 50% by weight) butene-2 (both cis and trans isomers) and typically comprises at least about 85% (e.g., from about 85% to about 100%) butene-2, as butene-2 is generally more selectively converted, relative to butene-1 and isobutylene, to the desired product (e.g., propylene) in the metathesis reactor or reaction zone. In some cases, it may be desirable to increase the butene-2 content of butylene, for example to achieve these ranges, by subjecting butylene to isomerization to convert butene-1 and isobutylene, contained in the butylene, to additional butene-2. The isomerization may be performed in a reactor that is separate from the reactor used for olefin metathesis. Alternatively, the isomerization may be performed in an isomerization reaction zone in the same reactor that contains an olefin metathesis reaction zone, for example by incorporating an isomerization catalyst upstream of the olefin metathesis catalyst or even by combining the two catalysts in a single catalyst bed. Suitable catalysts for carrying out the desired isomerization to increase the content of butene-2 in the butylene are known in the art and include, for example, magnesium oxide containing isomerization catalysts as described in U.S. Pat. No. 4,217,244.

As discussed above, the olefins may be derived from petroleum or non-petroleum sources. Crude oil refining operations yielding olefins, and particularly butylene, include hydrocarbon cracking processes carried out in the substantial absence of hydrogen, such as fluid catalytic cracking (FCC) and resid catalytic cracking (RCC). Olefins such as ethylene and butylene are recovered in enriched concentrations from known separations, including fractionation, of the total reactor effluents from these processes. Another significant source of ethylene is steam cracking, as discussed above. A stream enriched in ethylene is generally recovered from an ethylene/ethane splitter as a low boiling fraction, relative to the feed to the splitter, which fractionates at least some of the total effluent from the steam cracker and/or other ethylene containing streams. In the case of olefins derived from non-petroleum sources, both the ethylene and butylene, for example, may be obtained as products of an oxygenate to olefins conversion process, and particularly a methanol to light olefins conversion process. Such processes are known in the art, as discussed above, and optionally include additional conversion steps to increase the butylene yield such as by dimerization of ethylene and/or selective saturation of butadiene, as described in U.S. Pat. No. 7,568,018. According to various embodiments of the invention, therefore, at least a portion of the ethylene in the hydrocarbon feedstock is obtained from a low boiling fraction of an ethylene/ethane splitter and/or at least a portion of the butylene is obtained from an oxygenate to olefins conversion process.

With respect to the first and second olefins (e.g., ethylene and butylene) that undergo metathesis, the conversion level, based on the amount of carbon in these reactants that are converted to the desired product and by-products (e.g., propylene and heavier, $C_5^+$ hydrocarbons), is generally from about 40% to about 80% by weight, and typically from about 50% to about 75% by weight. Significantly higher conversion levels, on a "per pass" basis through the metathesis reactor or reaction zone, are normally difficult to achieve due to equilibrium limitations, with the maximum conversion depending on the specific olefin reactants and their concentrations as well as process conditions (e.g., temperature).

In one or more separations (e.g., fractionation) downstream of the metathesis reactor or reaction zone, the desired product (e.g., propylene) may be recovered in substantially pure form by removing and recovering unconverted olefins (e.g., ethylene and butylene) as well as reaction by-products (e.g., $C_5^+$ hydrocarbons including olefin oligomers and alkylbenzenes). Recycling of the unconverted olefin reactants back to the metathesis reactor or reaction zone may often be desirable for achieving complete or substantially complete overall conversion, or at least significantly higher overall conversion (e.g., from about 80% to about 100% by weight, or from about 95% to about 100% by weight) than the equilibrium-limited per pass conversion levels discussed above. The downstream separation(s) are normally carried out to achieve a high purity of the desired product, particularly in the case of propylene. For example, the propylene product typically has a purity of at least about 99% by volume, and often at least about 99.5% by volume to meet polymer grade specifications. According to other embodiments, the propylene purity may be lower, depending on the end use of this product. For example, a purity of at least about 95% (e.g., in the range from about 95% to about 99%) by volume may be acceptable for a non-polymer technology such as acrylonitrile production, or otherwise for polypropylene production processes that can accommodate a lower purity propylene.

At the per pass conversion levels discussed above, the selectivity of the converted feedstock olefin components (e.g., ethylene and propylene) to the desired olefin(s) (e.g., propylene) having an intermediate carbon number is generally at least about 75% (e.g., in the range from about 75% to about 100%) by weight, typically at least about 80% (e.g., in the range from about 80% to about 99%) by weight, and often at least about 90% (e.g., in the range from about 90% to about 97%) by weight, based on the amount of carbon in the converted products. The per pass yield of the desired olefin(s) is the product of the selectivity to this/these product(s) and the per pass conversion, which may be within the ranges discussed above. The overall yield, using separation and recycle of the unconverted olefin reactants as discussed above, can approach this/these product selectivity/selectivities, as essentially complete conversion is obtained (minus some purge and solution losses of feedstock and product(s), as well as losses due to downstream separation inefficiencies).

The conversion and selectivity values discussed above are achieved by contacting the hydrocarbon feedstock described above, either continuously or batchwise, with a catalyst as described herein. Generally, the contacting is performed with the hydrocarbon feedstock being passed continuously through a fixed bed of the catalyst in an olefin metathesis reactor or reaction zone. For example, a swing bed system may be utilized, in which the flowing hydrocarbon feedstock is periodically re-routed to (i) bypass a bed of catalyst that has become spent or deactivated and (ii) subsequently contact a bed of fresh catalyst. A number of other suitable systems for carrying out the hydrocarbon/feedstock contacting are known in the art, with the optimal choice depending on the particular feedstock, rate of catalyst deactivation, and other factors. Such systems include moving bed systems (e.g., countercurrent flow systems, radial flow systems, etc.) and fluidized bed systems, any of which may be integrated with continuous catalyst regeneration, as is known in the art.

Representative conditions for olefin metathesis (i.e., conditions for contacting the hydrocarbon feedstock and catalyst in the olefin metathesis reactor or reaction zone), in which the above conversion and selectivity levels may be obtained, include a temperature from about 75° C. (572° F.) to about 600° C. (1112° F.), and often from about 100° C. (752° F.) to about 500° C. (932° F.); a pressure from about 50 kPa gauge (7.3 psig) to about 8,000 kPa gauge (1160 psig), and often from about 1,500 kPa gauge (218 psig) to about 4,500 KPa gauge (653 psig); and a weight hourly space velocity (WHSV) from about 1 hr$^{-1}$ to about 10 hr$^{-1}$. As is understood in the art, the WHSV is the weight flow of the hydrocarbon feedstock divided by the weight of the catalyst bed and represents the equivalent catalyst bed weights of feed processed every hour. The WHSV is related to the inverse of the reactor residence time. Under the olefin metathesis conditions described above, the hydrocarbon feedstock is normally in the vapor phase in the olefin metathesis reactor or reaction zone, but it may also be in the liquid phase, for example, in the case of heavier (higher carbon number) olefin feedstocks.

The following examples are set forth to illustrate the invention. It is to be understood that the examples are only by way of illustration and are not intended as an undue limitation on the broad scope of the invention as set forth in the appended claims.

All experiments were carried out using standard Schlenk and glove-box techniques. Solvents were purified and dried according to standard procedures. SiO$_{2-(700)}$ was prepared from Aerosil™ silica from Degussa (specific area of 200 m$^2$/g), by partial dehydroxylation at 700° C. under high vacuum (10$^{-5}$ Torr) for 15 h to give a white solid having a specific surface area of 190 m$^2$/g and containing 0.7 OH nm$^{-2}$.

Example 1

Synthesis of W=OF(CH$_2$CMe$_3$)$_3$

The synthesis of [W=O(CH$_2$CMe$_3$)$_3$F] was carried out according to the following reaction.

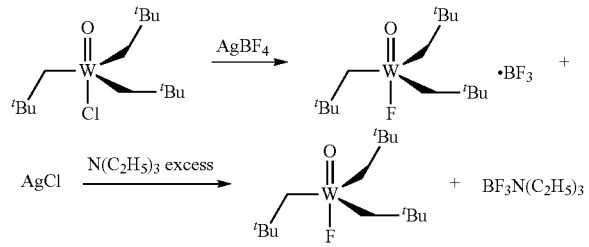

W=O(CH$_2$CMe$_3$)$_3$Cl was synthesized by the literature procedure (Schrock et. al., J. Am. Chem. Soc. 1984, 106, 6305-10). [W=O(CH$_2$CMe$_3$)$_3$Cl] (1.5 g, and AgBF$_4$ (0.65 g) were stirred in 20 mL of toluene for one hour at room temperature. The reaction mixture was filtered to remove the insoluble AgCl, and NEt$_3$ (1.1 mL) was added to remove the BF$_3$ moiety by precipitation as BF$_3$·N(C$_2$H$_5$)$_3$. The resulting solution was stirred for 16 h at room temperature and then filtered over celite. The solvent was then removed under vacuum to provide a white solid which was sublimed at 60° C. under reduced pressure (3.10-5 Torr) to yield 1.13 g of product. The product was analyzed and found to contain 41.47% C, 7.89% H and 4.72% F which agrees well with calculated percentages for C$_{15}$H$_{33}$OFW of 41.69% C, 7.69% H and 4.42% F.

Example 2

Synthesis of W(NPh)F(CH$_2$CMe$_3$)$_3$

W(NPh)F(CH$_2$CMe$_3$)$_3$ was synthesized by reaction of WOCl$_4$ with C$_6$H$_5$NCO, followed by alkylation with neopentyl magnesium chloride as shown below.

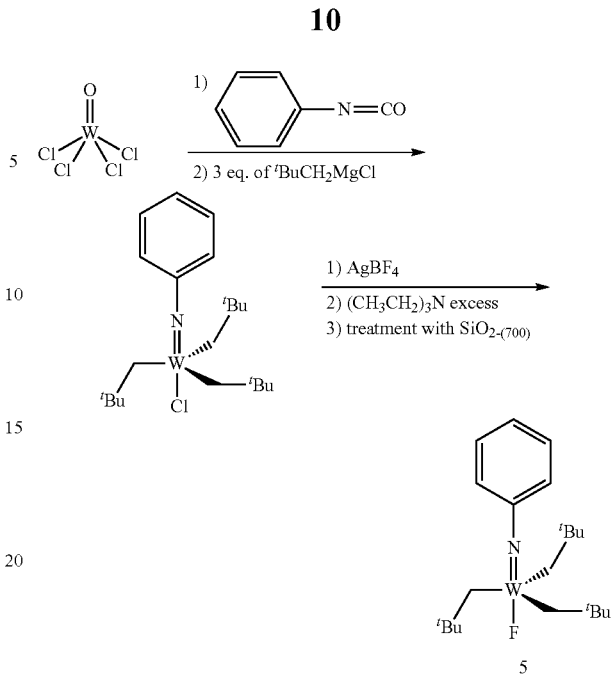

Freshly distilled phenylisocyanate (3.214 g) was added to a suspension of [W=OCl$_4$] (9.000 g) in 200 mL of heptane. This mixture was heated at reflux temperature for 4 days to provide a dark brown precipitate. The solvent was removed under vacuum and Et$_2$O (20 mL) was added resulting in a green solution mixture which was filtered to remove the insoluble impurities and Et$_2$O was then removed under vacuum producing a powder of dark green crystals of [W=N(C$_6$H$_5$)Cl$_4$].(Et$_2$O). A solution of 10.6 g [W=N(C$_6$H$_5$)Cl$_4$].(Et$_2$O) in toluene was prepared and stirred rapidly. This solution was cooled to −78° C. and to it there were added (dropwise) 30 mL of a 2.17 M ether solution of neopentylmagnesium chloride. The mixture was warmed up slowly to room temperature with continuous stirring at which point the solvent was removed under vacuum. The resulting product was extracted with pentane, and the extract was treated with activated carbon, stirred for 30 minutes, filtered through a bed of celite, and then the solvent was removed under vacuum. The yellow brown residue was collected on a frit, washed with chilled pentane and dried to give 3.8 g of [W=N(C$_6$H$_5$)(CH$_2$CMe$_3$)$_3$Cl] as a brown powder.

A portion of the [W=N(C$_6$H$_5$)(CH$_2$CMe$_3$)$_3$Cl] (2.000 g) obtained above and 0.74 g of AgBF$_4$ were stirred in 20 mL of toluene for one hour at room temperature. The reaction mixture was filtered to remove the insoluble AgCl, and 1.1 mL of NEt$_3$ was added. The resulting solution was stirred for 16 h at room temperature, filtered over celite and the solvent then removed under vacuum to provide a yellow pale solid. The product still contained boron as observed by $^{11}$B NMR. A solution of the product in pentane was added to SiO$_{2-(700)}$ (500 mg) and reacted for 4 hours. The silica was extracted 3 times with pentane, the solutions combined and the solvent was then removed under vacuum to provide a yellow pale solid. This product was sublimed at 60° C. under reduced pressure (3×10$^5$ Torr) to yield 580 mg of pure product. The product was analyzed and found to contain 48.86% C, 7.38% H, 4.54% F; 2.74% N and 34.90% W which agrees well with calculated percentages for C$_{21}$H$_{38}$FNW of 49.71% C, 7.55% H, 3.74% F; 2.76% N and 36.23% W.

Example 3

Synthesis of WOF(CH$_2$CMe$_3$)$_3$/SiO$_2$

A mixture of the product of Example 1 [WO(CH$_2$CMe$_3$)$_3$F] (500 mg) in pentane (10 mL) and SiO$_{2\text{-}(700)}$ (2 g) was stirred at 25° C. overnight. After filtration, the solid was washed 5 times with pentane and all volatile compounds were condensed into another reactor (of known volume) in order to quantify neopentane evolved during grafting. The resulting white powder was dried under vacuum (10$^{-5}$ Torr). Analysis by gas chromatography indicated the formation of 290 μmol of neopentane during the grafting (1.0±0.1 NpH/W). Elemental analysis showed: W 4.43 wt-%; C 3.27 wt-%.

Example 4

Synthesis of W(NPh)F(CH$_2$CMe$_3$)$_3$/SiO$_2$

A mixture of the product of Example 2 (500 mg), SiO$_{2\text{-}(700)}$ (2 g) and pentane (10 mL) was stirred at 25° C. overnight. After filtration, the solid was washed 5 times with pentane. The resulting white powder was dried under vacuum (10$^{-5}$ Torr). Elemental analysis: W 4.8 wt-%; C 6.5 wt-%; N 0.5 wt-%.

Example 5

Catalytic Testing in Propylene Metathesis of the Catalyst of Example 3

A stainless-steel half-inch cylindrical reactor that can be isolated from ambient atmosphere was charged with 128 mg of the catalyst of Example 3 in a glovebox. After connection to the gas lines and purging of the tubing, a 20 ml/min flow of purified propylene was passed over the catalyst bed at 80° C. Hydrocarbon products were analyzed online by GC. At 30 hours on stream, the catalyst exhibited a total turn over number of 8300. Selectivity was 50% to ethylene and 50% to 2-butenes. The E/Z ratio of the 2-butene formed was 1.5.

Example 6

Catalytic Testing in Propylene Metathesis of the Catalyst of Example 4

A stainless-steel half-inch cylindrical reactor that can be isolated from ambient atmosphere was charged with 135 mg of the catalyst of Example 4 in a glovebox. After connection to the gas lines and purging of the tubing, a 20 ml/min flow of purified propylene was passed over the catalyst bed at 80° C. Hydrocarbon products were analyzed online by GC. At 30 hours on stream, the catalyst exhibited a total turn over number of 1150. Selectivity was 50% to ethylene and 50% to 2-butenes. The E/Z ratio of the 2-butene formed was 0.9.

The invention claimed is:

1. A catalyst comprising a tungsten metal compound for metathesis of olefins characterized in that it contains at least one tungsten-fluorine bond, the compound dispersed on a refractory oxide support wherein the compound is chemically bonded to the support and wherein the tungsten containing compound is selected from the group consisting of WR$_4$F, WOFR$_3$, W(NR')FR$_3$ and mixtures thereof and where "R" is an organic group which does not have any hydrogen atoms beta to the tungsten and R' is an organic group selected from the group consisting of H, phenyl, 2,6-dimethylphenyl and methyl.

2. The catalyst of claim 1 where R is selected from the group consisting of neopentyl (—CH$_2$CMe$_3$); methyl, 2,2-diethylpropyl (—CH$_2$C(CH$_2$CH$_3$)$_2$Me), and 2,2-diethylbutyl (—CH$_2$C(CH$_2$CH$_3$)$_2$CH$_2$CH$_3$).

3. The catalyst of claim 1 where the tungsten-metal compound is present in an amount from about 0.5 to about 10 wt-% of the catalyst as the metal.

4. The catalyst of claim 1 where the refractory oxide support is selected from the group consisting of silica, aluminas, silica-aluminas, titania, zirconia and mixtures thereof.

5. The catalyst of claim 4 where the refractory oxide is silica.

6. The catalyst of claim 5 where the silica is an acid washed silica.

7. The catalyst of claim 1 where the refractory oxide support has a surface area of at least 50 m$^2$/g.

8. The catalyst of claim 7 where the refractory oxide support has a surface area from about 80 to about 500 m$^2$/g.

* * * * *